US00PP18178P3

(12) United States Plant Patent
Zaiger et al.

(10) Patent No.: US PP18,178 P3
(45) Date of Patent: Nov. 6, 2007

(54) INTERSPECIFIC TREE NAMED 'DAPPLE JACK'

(50) Latin Name: **Interspecific *Prunus* species**
Varietal Denomination: Dapple Jack

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 32 days.

(21) Appl. No.: 11/395,646

(22) Filed: Apr. 3, 2006

(65) Prior Publication Data

US 2007/0234446 P1 Oct. 4, 2007

(51) Int. Cl.
*A01H 5/00* (2006.01)

(52) U.S. Cl. ..... Plt./180

(58) Field of Classification Search ..... Plt./180
See application file for complete search history.

*Primary Examiner*—Kent Bell
*Assistant Examiner*—S. B. McCormick-Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of fruit.
2. Fruit with excellent flavor and eating quality.
3. Fruit having good balance between acid and sugar with an average Brix of 21.3°.
4. Fruit having an attractive red flesh color.
5. The tree having a vigorous, upright growth habit.

1 Drawing Sheet

Botanical classification: Interspecific *Prunus* species.

BACKGROUND OF THE VARIETY

FIELD OF THE INVENTION

In the field of plant genetics, we conduct an extensive and continuing plant-breeding program, including the organization and asexual reproduction of orchard trees, and of which plums, peaches, nectarines, apricots, cherries, almonds and interspecifics are exemplary. It was against this background of our activities that the present variety of interspecific tree was originated and asexually reproduced in our experimental orchard located near Modesto, Stanislaus County, Calif.

PRIOR VARIETIES

Among the existing varieties of plum, apricot and interspecific trees, which are known to us, and mentioned herein, 'Friar' Plum (not-patented), 'Autumn Giant' Plum (U.S. Plant Pat. No. 5,624), 'Mariposa' Plum (U.S. Plant Pat. No. 111), 'Red Beaut' Plum (U.S. Plant Pat. No. 2,539), 'Modesto' Apricot (U.S. Plant Pat. No. 2,543), 'Autumn Glory' Apricot (not-patented) 'Splash' Interspecific (U.S. Plant Pat. No. 14,583), and 'King' Apricot (non-patented).

ORIGIN OF THE VARIETY

The new and distinct interspecific tree was originated by us from crosses between the following species [*Prunus salicina, Prunus armeniaca* and (*Prunus salicinia*×*Prunus armeniaca*)]. The present variety was selected from seedlings of an open pollinated proprietary interspecific tree with field identification number '20Z62', which was developed by us from multiple crosses between the following varieties; 'Friar' Plum (non-patented), 'Autumn Giant' Plum (U.S. Plant Pat. No. 5,624), 'Mariposa' Plum (U.S. Plant Pat. No. 111), 'Red Beaut' Plum (U.S. Plant Pat. No. 2,539), 'King' Apricot (non-patented), 'Modesto' Apricot (U.S. Plant Pat. No. 2,543), 'Autumn Glory' Apricot (non-patented) and 'Splash' Interspecific (U.S. Plant Pat. No. 14,583). We budded a large number of these open pollinated seedlings to older 'Nemaguard' Rootstock (non-patented) trees to induce earlier fruit production, and under close and careful observation, the present variety exhibited desirable fruit characteristics and was selected in 2000 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree, which includes plums, apricots and plumcots in its parentage is of large size, vigorous, upright growth and a regular and productive bearer of large, red flesh fruit with excellent flavor and eating quality. The fruit is further characterized by being nearly globose in shape, with an attractive speckled red skin color, the flesh having an excellent balance between acid and sugar with an average Brix of 21.3°. In comparison to the proprietary interspecific maternal parent (20Z62), the new interspecific variety matures in the same maturity time, has red flesh compared to yellow and has speckled red skin color compared to blue. In comparison to the interspecific tree 'Splash' (U.S. Plant Pat. No. 14,583), the new variety has larger fruit, red skin and flesh color compared to yellow skin and flesh color and is approximately 2 weeks later in maturity.

PHOTOGRAPHS OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 5 years of age, its flowers, foliage and fruit, as based on observations of 5 year old specimens grown near Modesto, Calif., with color in accordance with Munsell Book of Color.

Tree:

*Size.*—Large, pruned to approximately 3 to 3.5 meters in height for economical harvesting of fruit. Average spread 3 meters, varies with different cultural practices.

*Vigor.*—Vigorous, tree growth of approximately 1 to 1.5 meters the first growing season, varies with soil type, fertility and cultural practices.

*Form.*—Upright, usually pruned to vase shape.

*Branching habit.*—Upright, crotch angle approximately 30° increases with heavy crop load.

*Productivity.*—Productive, usually sets 1½ to several times more fruit than desired, thinning and spacing of fruit necessary. Fruit set varies with climatic conditions at bloom time.

*Bearer.*—Regular, adequate fruit set 3 consecutive years, no alternate bearing observed.

*Fertility.*—Self sterile, pollinator required.

*Density.*—Medium dense. Usually pruned to vase shape to allow sunlight to center of tree to enhance fruit color and health of fruit spurs.

*Hardiness.*—Tree grown in USDA Hardiness Zone 9. Hardy in all stone fruit growing areas of California. Winter chilling requirement approximately 700 hours at or below 45° F.

Trunk:

*Size.*—Large. Average circumference 55.9 cm at 17.8 cm above ground level on 5 year old trees.

*Texture.*—Medium shaggy, increases with age of tree.

*Color.*—Varies from 5Y 4/2 to 7.5Y 5/2.

Branches:

*Size.*—Medium. Average circumference 13.7 cm at 1.2 meters above ground level. Crotch angle approximately 30°, increases with heavy crop load.

*Surface Texture.*—New growth smooth, mature growth medium rough, roughness increases with age.

*Lenticels.*—Numerous, average number 52 in a 25.8 square cm area. Average length 3.6 mm. Average width 1.3 mm. Color varies from 5YR 6/8 to 7.5YR 6/10.

*Color.*—New growth varies from 2.5GY 7/8 to 5GY 6/6. Mature growth varies from 5YR 4/4 to 7.5YR 4/4, varies with age of growth.

Leaves:

*Size.*—Medium. Average length 101.2 mm. Average width 39.7 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, surface glabrous. Lower surface relatively smooth, except for small ridges created by midrib and pinnate venation, surface glabrous.

*Petiole.*—Medium. Average length 11.1 mm. Average width 1.1 mm. Color varies from 5GY 6/6 to 5GY 5/6. Longitudinally grooved. Surface— glabrous.

*Glands.*—Type— globose. Size— small. Average length 0.4 mm. Average diameter 0.3 mm. Average number one, varies from 0 to 2. Located primarily on base of leaf blade and upper portion of petiole. Color varies from 7.5R 4/10 to 2.5GY 7/6.

*Color.*—Upper surface varies from 5GY 4/6 to 7.5GY 3/6. Lower surface varies from 5GY 5/4 to 7.5GY 4/4. Midvein color varies from 2.5GY 8/4 to 5GY 8/4.

Flower buds:

*Size.*—Small to medium. Average length 8.7 mm. Average width 4.9 mm.

*Hardiness.*—Hardy in all stone fruit growing areas of California.

*Form.*—Conical, becoming slightly elongated just before opening.

*Pedicel.*—Size— medium. Average length 14.3 mm. Average width 0.4 mm. Color varies from 2.5GY 8/6 to 2.5GY 7/8.

*Color.*—N 9.5/ (white).

*Number of buds per spur.*—Average number 3, varies from 2 to 6. Varies with age of spur.

Flowers:

*Size.*—Small to medium. Average height 9.5 mm. Average diameter 17.7 mm.

*Petals.*—Number— 5, alternately arranged to sepals. Size— small to medium. Average length 8.8 mm. Average width 7.0 mm. Form— obovate. Margin— sinuate. Both upper and lower surfaces glabrous. Color N 9.5/ (white).

*Sepals.*—Number 5, alternately arranged to petals. Size— small. Average length 2.7 mm. Average width 2.6 mm. Form— ovate, apex rounded. Margin— entire. Both upper and lower surfaces glabrous. Color— lower surface varies from 5GY 7/6 to 5GY 6/8. Upper surface varies from 2.5GY 8/6 to 5GY 7/6.

*Stamens.*—Average number per flower— 39. Average filament length 7.0 mm. Filament color N 9.5/ (white). Anther color varies from 5Y 8.5/10 to 5Y 8/10.

*Pollen.*—Abundant. Self sterile, pollinator required. Color varies from 2.5Y 7/12 to 5Y 7/10.

*Pistil.*—Normally one. Surface— glabrous. Average length 6.8 mm. Position of stigma— average of 1.9 mm below anthers. Color varies from 10Y 8.5/6 to 2.5GY 8/6.

*Fragrance.*—Slight.

*Blooming Period.*—Date of First Bloom Feb. 24, 2005. Date of Petal Fall Mar. 3, 2005, varies slightly with climatic conditions.

*Color.*—N 9.5/ (white).

*Number flowers per flower bud.*—Average number 2, varies from one to three.

*Pedicel.*—Size— medium. Average length 15.8 mm. Average width 0.5 mm. Color varies from 2.5GY 9/6 to 2.5GY 7/8. Surface— glabrous.

Fruit:

*Maturity when described.*—Firm ripe.

*Date of first picking.*—Jul. 7, 2005.

*Date of last picking.*—Jul. 12, 2005, varies slightly with climatic conditions.

*Size.*—Large. Average diameter axially 58.9 mm. Average transversely in suture plane 62.0 mm. Average weight 144.8 grams, varies slightly with fertility of the soil, amount of thinning and climatic conditions.

*Form.*—Globose.

*Suture.*—Nearly smooth, extends from base to apex.

*Ventral surface.*—Relatively smooth, some fruit slightly lipped.

*Apex.*—Varies from rounded to slight tip.

*Base.*—Slightly retuse.

*Cavity.*—Rounded to slightly elongated in suture plane. Average depth 5.9 mm. Average diameter 8.7 mm.

Stem:

*Size.*—Large. Average length 16.3 mm. Average diameter 1.9 mm.

*Color.*—Varies from 2.5GY 6/6 to 2.5GY 5/8.

Flesh:

*Ripens.*—Evenly.

*Texture.*—Firm, meaty.

*Fibers.*—Few, small, tender.

*Firmness.*—Firm, comparable to 'Red Beaut' Plum (U.S. Plant Pat. No. 2,539).

*Aroma.*—Slight.

*Amydgalin.*—Undetected.

*Eating quality.*—Excellent.

*Flavor.*—Excellent, good balance between acid and sugar.

*Juice.*—Moderate, enhances flavor.

*Brix.*—Average 21.3°, varies slightly with amount of fruit per tree and climatic conditions.

*Color.*—Varies from 5R 4/10 to 2.5R 3/10. Pit cavity varies from 2.5R 2/8 to 5R 2/8.

Skin:

*Thickness.*—Medium.

*Surface.*—Smooth.

*Bloom.*—Moderate amount, complete coverage.

*Tendency to crack.*—None.

*Color.*—Ground color varies from 5Y 6/4 to 7.5Y 6/4. Overspread with 2.5R 3/4 to 2.5R 2/6. Small, randomly spaced areas of ground color exposed to skin surface giving a speckling pattern to skin.

*Tenacity.*—Tenacious to flesh.

*Astringency.*—Undetected.

Stone:

*Type.*—Clingstone.

*Size.*—Medium. Average length 25.7 mm. Average width 19.2 mm. Average thickness 12.3 mm.

*Form.*—Obovoid.

*Base.*—Usually flat, varies from flat to rounded.

*Apex.*—Pointed. Average length 1.2 mm.

*Surface.*—Slightly pitted throughout, one shallow, long groove on each side of suture creating a small, narrow ridge running the length of the suture. Some stones have a low, narrow ridge near the center of the stone extending from base to apex.

*Sides.*—Unequal, with one side extending further outward from the suture plane.

*Tendency to split.*—Very slight.

*Color.*—Various from 7.5YR 5/6 to 10YR 6/6, when dry.

Kernal:

*Form.*—Ovate.

*Viability.*—Viable, complete embryo development.

*Size.*—Medium. Average length 14.2 mm. Average width 9.8 mm. Average depth 5.4 mm.

*Skin color.*—Varies from 5Y 9/6 to 5Y 8/8.

Use: Dessert. Market— local and long distance.

Keeping Quality: Good, held firm for 10 days in cold storage at 38° to 42° F. without internal breakdown of flesh, or appreciable loss of flavor.

Shipping quality: Good, showed minimal skin scarring or flesh bruising of fruit in picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of large, firm, red flesh fruit with excellent flavor and eating quality; the fruit is further characterized by having a good balance between acid and sugar with an average Brix of 21.3° and in comparison to its proprietary interspecific maternal parent (20Z62), which has fruit maturing in the same season with yellow flesh and blue skin color, the new variety has red flesh and skin color.

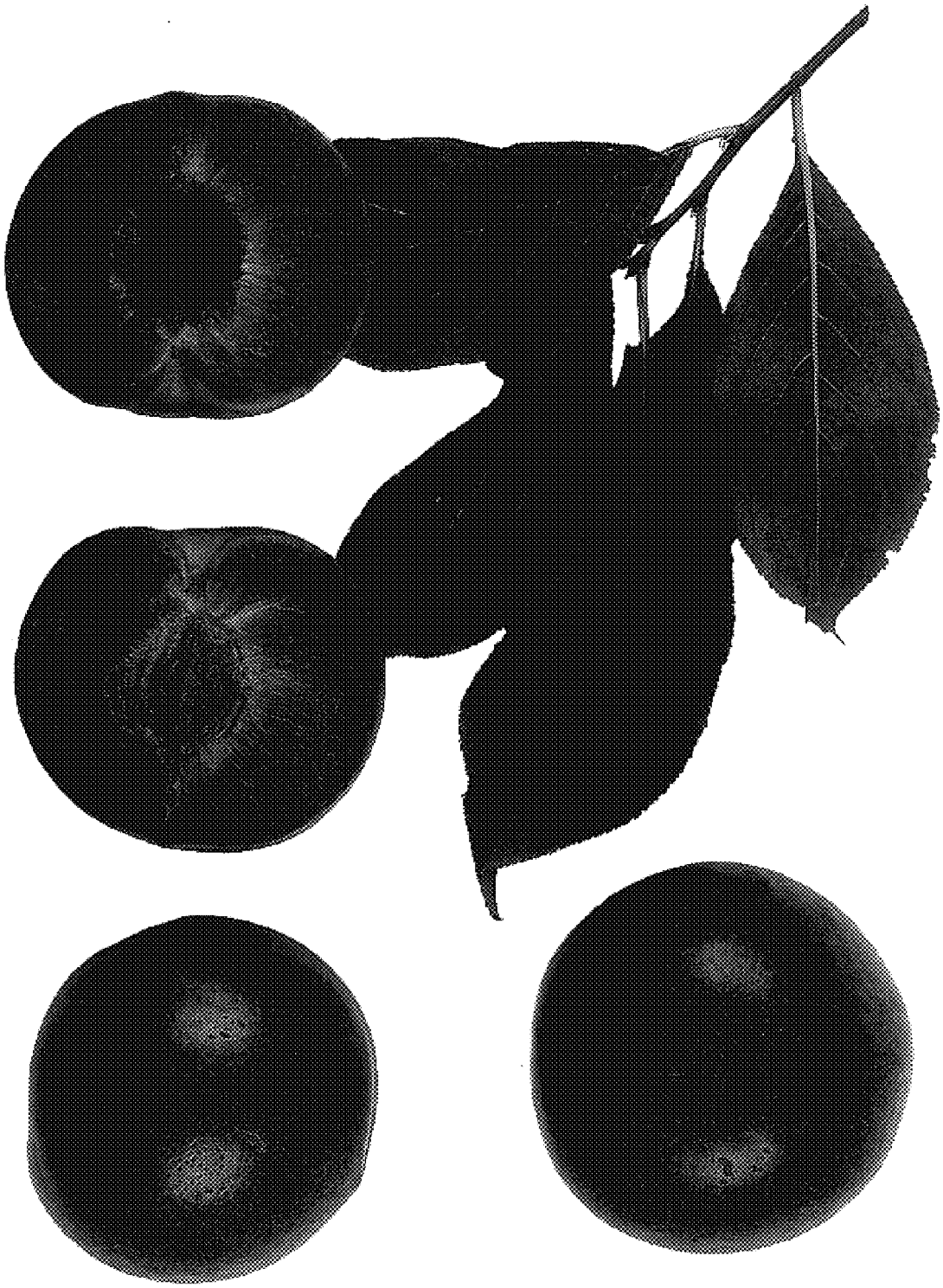

* * * * *